July 28, 1942. S. TARNOK Plant Pat. 536
BUDDLEIA PLANT
Filed Feb. 16, 1942
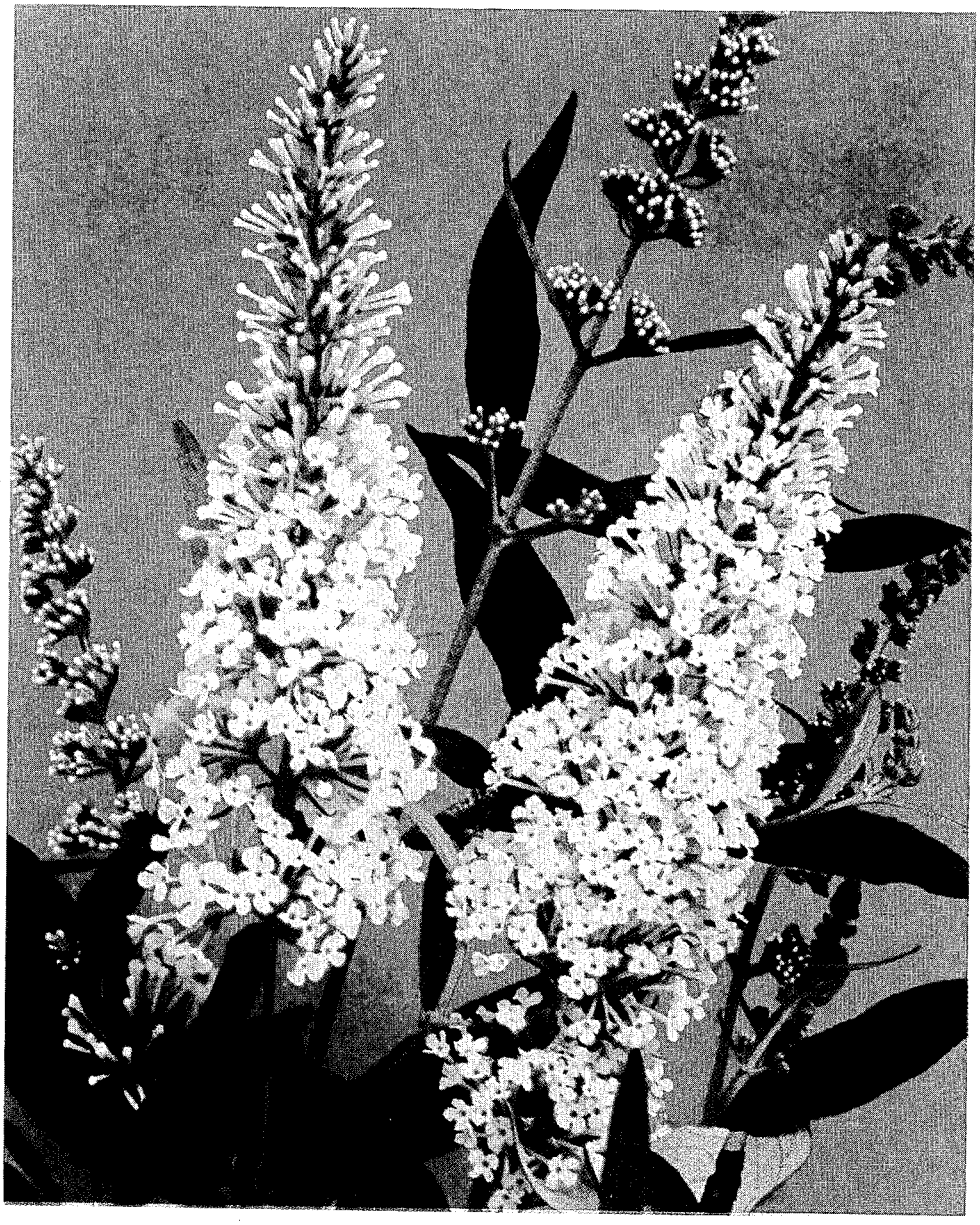
Inventor
S. Tarnok
By Robbe Robb
attorneys Patented July 28, 1942

Plant Pat. 536

UNITED STATES PATENT OFFICE

536

BUDDLEIA PLANT

Sigmund Tarnok, Slidell, La., assignor to Jackson & Perkins Company, Newark, N. Y., a corporation of New York Application February 16, 1942, Serial No. 431,140

1 Claim. (Cl. 47—60)

The present invention relates to a new and distinct variety of Buddleia plant, originating as a seedling of an unnamed seedling, in turn originating from a light bud sport of "Ile de France."

The attractiveness and habits of this new Buddleia fill an important place in the class of decorative plants, because this new variety serves excellently the purposes as a florist's cut flower and as a garden decoration plant.

In the place where these observations have been made, at Newark, New York, the new variety grows upright, spreading somewhat like Ile de France, to a height of 5 feet, and it is as hardy as Ile de France.

While the characteristics of its foliage, as hereinafter set forth, are important, it is in the flowers produced by the plant that the primary distinctiveness and novelty exist. These flowers are produced on spikes ranging from 6 to 8 inches in length and are composed of numerous small flowers of glistening pure white color (Plate 53, Ridgway's Chart) with a very slight suggestion of Maize Yellow (Plate 4).

The salver-shaped corolla consists of a tube which is Maize Yellow (Plate 4) and 4 or 5 segments which are a pure white with an apparent reflection of Apricot Yellow (Plate 4) caused by the pollen inside of the tube. The outside of the tube is Maize Yellow (Plate 4). This pure white color of the blossom is entirely new in a hardy Buddleia plant.

The flower starts blooming from the bottom as is the habit of most of these Buddleia varieties, but the lower flowers retain their shape and color until the very tip of the spike is open. This substantially all-out-at-once blooming characteristic is rare in Buddleias and makes for value of the new variety both in its adaptability to cut flower purposes and garden decoration.

In the accompanying illustration the flower is shown in its different stages of development, and in one it will be noted that the blooms of the individual flowers at the base of the panicle are still in their beauty as the flowerets of the tip portion are about to open. When the flowerets, which cover the stem completely, are in full bloom they make a complete round or circular panicle of great attractiveness and these flowers are very fragrant.

It will also be noted in the illustration that the buds shown are Absinthe Green in color (Plate 31) with the tip a Pale Glass Green (Plate 31).

The following may be taken as a detailed description of the foliage of the plant:

New foliage: Upper side, Light Cress Green, Plate 31, under side, Pale Fluorite Green, Plate 32.

Old foliage: Upper side, Elm Green, Plate 17, under side, Light Cress Green, Plate 31, with a silvery sheen. As the leaf gets older, this silvery sheen becomes more dominant.

*Shape.*—Lanceolate.

*Texture.*—Smooth upper side. Rough under side.

*Ribs and veins.*—Prominent.

*Edge.*—Serrated, single and deep.

*Leaf stem.* — *Color* — Light Turtle Green, Plate 32. Under side—smooth.

Wood:

*New wood.* — Absinthe Green, Plate 31. Bark—smooth.

*Old wood.*—Light Cress Green, Plate 31, and pubescent.

By way of summary, it may be again noted that the white color of the blossoms of this variety is its principal characteristic when taken in conjunction with the fact that it is the first hardy variety of this color. The secondary novel characteristic of this variety is the all-out-at-once blooming habit which is very scarce in these plants, having particular reference to Buddleias of the white color. It is distinguished from *Buddleia Asiatica* in that the latter is not considered to be hardy and is of a weeping type of growth, the foliage being more pubescent and silvery and has less green cast to it. The fragrance is entirely different. This new variety therefore presents an important step in advance among plants of this class.

I claim:

A new and distinct variety of Buddleia plant, characterized as to novelty by its habit of growth, hardiness, round shape and pure white coloring of its panicles and the habit of opening of the flowerets throughout the complete length of the panicle before fading starts, substantially as shown and described.

SIGMUND TARNOK.